United States Patent
Yang et al.

(10) Patent No.: US 10,342,455 B2
(45) Date of Patent: Jul. 9, 2019

(54) METHOD AND DEVICE FOR DETECTING PHYSIOLOGICAL INFORMATION

(71) Applicant: ASUSTeK COMPUTER INC., Taipei (TW)

(72) Inventors: Hung-Yu Yang, Taipei (TW); Shou-Wei Chen, Taipei (TW)

(73) Assignee: ASUSTeK COMPUTER INC., Taipei (TW)

( * ) Notice: Subject to any disclaimer, the term of this patent is extended or adjusted under 35 U.S.C. 154(b) by 551 days.

(21) Appl. No.: 15/013,954

(22) Filed: Feb. 2, 2016

(65) Prior Publication Data
US 2016/0235308 A1    Aug. 18, 2016

(30) Foreign Application Priority Data
Feb. 13, 2015 (CN) .......................... 2015 1 0078171

(51) Int. Cl.
*A61B 5/08* (2006.01)
*A61B 5/024* (2006.01)
*A61B 5/11* (2006.01)
*A61B 5/00* (2006.01)

(52) U.S. Cl.
CPC ............ *A61B 5/0816* (2013.01); *A61B 5/024* (2013.01); *A61B 5/7282* (2013.01); *A61B 5/02438* (2013.01); *A61B 5/11* (2013.01)

(58) Field of Classification Search
CPC ..... A61B 5/0816; A61B 5/024; A61B 5/7282; A61B 5/02438; A61B 5/11; A61B 5/1107; A61B 5/113; A61B 5/1135

USPC .................. 600/481, 483, 484, 595
See application file for complete search history.

(56) References Cited

U.S. PATENT DOCUMENTS

| | | | |
|---|---|---|---|
| 6,889,553 B2 * | 5/2005 | Robinson ................. | G01H 1/14 73/649 |
| 8,562,526 B2 | 10/2013 | Heneghan et al. | |
| 9,138,153 B2 * | 9/2015 | Narusawa .......... | A61B 5/02416 |
| 9,354,447 B2 * | 5/2016 | Abdollahi ............ | A42B 3/0433 |
| 9,510,775 B2 * | 12/2016 | Morren ................ | A61B 5/1102 |
| 9,934,668 B2 * | 4/2018 | Zhang .................. | A61B 5/7246 |
| 2005/0011266 A1 * | 1/2005 | Robinson ................. | G01H 1/14 73/649 |
| 2006/0084848 A1 * | 4/2006 | Mitchnick .......... | A61B 5/14539 600/301 |

(Continued)

FOREIGN PATENT DOCUMENTS

| CN | 101489478 | 7/2009 |
| CN | 102458246 | 5/2012 |
| CN | 203252647 | 10/2013 |

*Primary Examiner* — Navin Natnithithadha
(74) *Attorney, Agent, or Firm* — JCIPRNET

(57) ABSTRACT

A method for detecting physiological information, adapted to a wearable multi-axis accelerometer for detecting the physiological information, the method comprises obtaining a detecting signal in a sampling time via the multi-axis accelerometer; detecting peaks of the detecting signal in a first searching time interval to obtain a plurality of first peaks; calculating first time intervals between every two adjacent first peaks, and taking maximum of the first time intervals as a second searching time interval; detecting peaks of the detecting signal in the second searching time intervals to obtain a plurality of the second peaks; and obtaining the physiological information from the detecting signal based on the second peaks.

14 Claims, 10 Drawing Sheets

(56) References Cited

U.S. PATENT DOCUMENTS

| | | | |
|---|---|---|---|
| 2009/0192418 A1* | 7/2009 | Miyashita | A61B 5/1101 600/595 |
| 2009/0209875 A1 | 8/2009 | Giorgis et al. | |
| 2011/0208016 A1* | 8/2011 | Bombardini | A61B 5/021 600/301 |
| 2012/0004563 A1 | 1/2012 | Kim et al. | |
| 2012/0065524 A1* | 3/2012 | Morren | A61B 5/1102 600/484 |
| 2012/0249766 A1* | 10/2012 | Narusawa | A61B 5/02416 348/77 |
| 2013/0044043 A1* | 2/2013 | Abdollahi | A42B 3/0433 345/8 |
| 2013/0109989 A1* | 5/2013 | Busse | A61B 5/1102 600/527 |
| 2013/0110415 A1* | 5/2013 | Davis | A42B 3/046 702/41 |
| 2013/0123665 A1* | 5/2013 | Mariani | A61B 5/1038 600/592 |
| 2014/0288442 A1* | 9/2014 | Bombardini | A61B 5/0205 600/484 |

* cited by examiner

METHOD AND DEVICE FOR DETECTING PHYSIOLOGICAL INFORMATION

CROSS-REFERENCE TO RELATED APPLICATION

This application claims the priority benefit of China application serial No. 201510078171.0, filed on Feb. 13, 2015. The entirety of the above-mentioned patent application is hereby incorporated by references herein and made a part of specification.

BACKGROUND OF THE INVENTION

Field of the Invention

The disclosure relates to a method for detecting physiological information and, more particularly, relates to a method and a device for detecting physiological information using a multi-axis accelerometer.

Description of the Related Art

In general heart rate detecting methods using a mobile electronic device and a wearable device include the following three ways. One way is to use a rear lens at the mobile electronic device. That is, when a user covers the rear lens with his finger, the finger is illuminated by a flash light during the detection, and his heart rate is estimated based on the variations in brightness of the finger image taken by the rear lens.

Another way is to use a front lens at the wearable device for detecting the user's face. When a face image is detected, the user should stand still, and the heart rate is estimated based on the variations in color at the region of interest (ROI) in the face image.

Still another way is to use the mobile electronic device or the wearable device equipped with a sensor (such as a light emitting diode and a photodiode) for detecting the heart rate. During the detection, the sensor is contacted with the user's finger(s) or the skin of an auir, and the heart rate is estimated based on the amount of the light received by the sensor.

BRIEF SUMMARY OF THE INVENTION

According to a first aspect of the present disclosure, A method for detecting physiological information, adapted to a wearable multi-axis accelerometer for detecting the physiological information, the method comprises obtaining a detecting signal in a sampling time via the multi-axis accelerometer; detecting peaks of the detecting signal in a first searching time interval to obtain a plurality of first peaks; calculating first time intervals between every two adjacent first peaks, and taking maximum of the first time intervals as a second searching time interval; detecting peaks of the detecting signal in the second searching time intervals to obtain a plurality of the second peaks; and obtaining the physiological information from the detecting signal based on the second peaks.

According to a second aspect of the present disclosure, a wearable physiological information detecting device, comprising: a multi-axis accelerometer; and a processing unit coupled to the multi-axis accelerometer and executing a plurality of modules, wherein the modules include: a signal-obtaining module for obtaining a detecting signal in a sampling time via the multi-axis accelerometer; a peak-detecting module configured to detect peaks of the detecting signal in a first searching time interval to obtain a plurality of first peaks, calculate first time intervals between every two adjacent first peaks to take the maximum of the first time intervals as a second searching time interval, and detect peaks of the detecting signal in the second searching time interval to obtain a plurality of second peaks; and a physiological information estimation module for obtaining the physiological information from the detecting signal based on the second peaks.

According to a third aspect of the present disclosure, A physiological information detecting system, comprising: a wearable device for detecting physiological information, including: a multi-axis accelerometer for generating an acceleration data in a sampling time; and a first communication unit coupled to the multi-axis accelerometer; and a mobile electronic device including: a second communication unit connected with the first communication unit; a processing unit coupled to the second communication unit, receiving the acceleration data from the wearable device via the second communication unit, and executing a plurality of modules, wherein the modules include: a signal-obtaining module for obtaining a detecting signal from the acceleration data; a peak-detecting module configured to detect peaks of the detecting signal in a first searching time interval to obtain a plurality of first peaks, calculate a first time interval between every two adjacent first peaks to take maximum of the first time intervals as a second searching time interval, and detect peaks of the detecting signal in the second searching time interval to obtain a plurality of second peaks; and a physiological information estimation module for obtaining the physiological information from the detecting signal based on the second peaks.

BRIEF DESCRIPTION OF THE DRAWINGS

These and other features, aspects and advantages of the disclosure will become better understood with regard to the following embodiments and accompanying drawings.

DETAILED DESCRIPTION OF THE EMBODIMENTS

Figure 1:
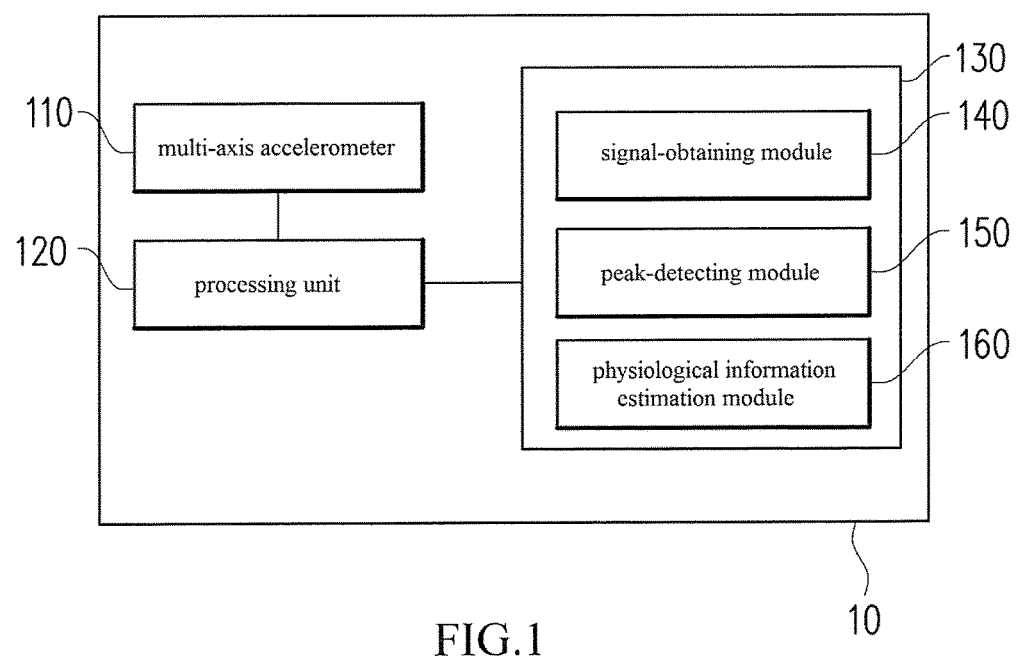
FIG. 1 is a block diagram of a physiological information detecting device in an embodiment.

FIG. 1 is a block diagram of a physiological information detecting device in an embodiment. Referring to FIG. 1, in an embodiment, the physiological information detecting device 10 is, but not limited to, a mobile electronic device or a wearable device worn by a user for detecting physiological information. In the embodiment, the physiological information detecting device 10 includes a multi-axis accelerometer 110, a processing unit 120 and a storage unit 130. The processing unit 120 is coupled to the multi-axis accelerometer 110 and the storage unit 130.

In an embodiment, the multi-axis accelerometer 110 is a three-axis accelerometer (which is also called as a gravity accelerometer) for detecting a gravitational acceleration (G-force) of a moving object in a three-dimensional XYZ space and generating a corresponding acceleration data.

In an embodiment, the processing unit 120 is a CPU (Central Processing Unit) with a single core or multiple cores. In an embodiment, the processing unit 120 is, but not limited to, a microprocessor or a signal processor that is programmable for general/special use.

In an embodiment, the storage unit 130 is one or a combination of a RAM, a ROM, a flash memory, a hard disk, and the storage unit 130 is removable or unremovable. The storage unit 130 is used for storing multiple functional modules executed by the processing unit 120. In an embodiment, the functional module is a signal-obtaining module 140, a peak-detecting module 150 and a physiological information estimation module 160. In an embodiment, these modules are programs executed by the processing unit 120 for the detection of the physiological information. In an embodiment, the signal-obtaining module 140, the peak-detecting module 150 and the physiological information estimation module 160 are hardware including multiple digital logic gates. In an embodiment, the signal-obtaining module 140, the peak-detecting module 150 and the physiological information estimation module 160 are, but not limited to, processors, respectively.

Figure 2:
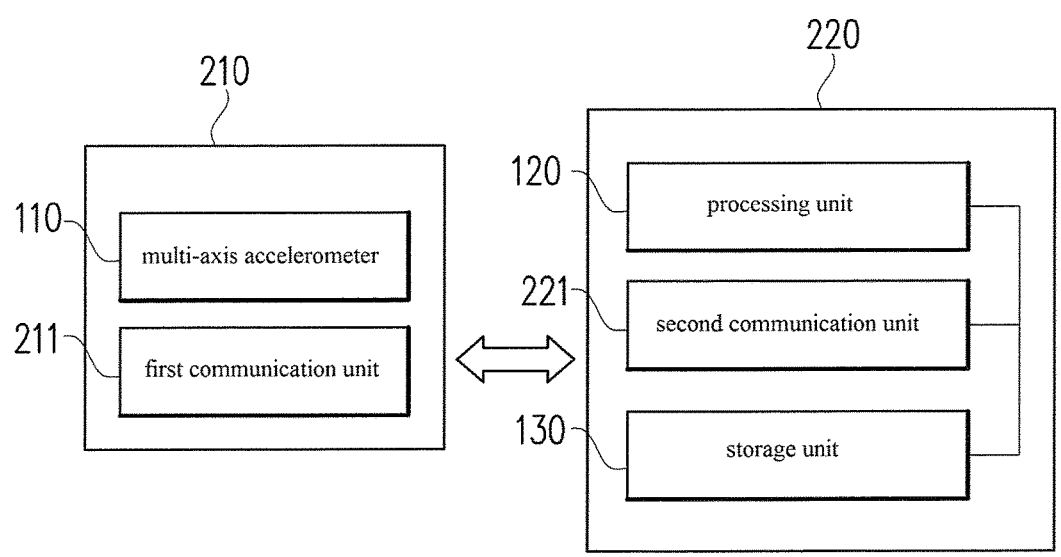
FIG. 2 is a block diagram of a physiological information detecting system in an embodiment.

FIG. 2 is a block diagram of a physiological information detecting device in an embodiment. Referring to FIG. 2, in the embodiment, the physiological information detecting system 20 includes a separate wearable device 210 and a mobile electronic device 220 which are separate from each other. The similar component in FIG. 2 as that in the physiological information detecting device 10 denotes by a same number, and the description is omitted herein.

The wearable device 210 includes a multi-axis accelerometer 110 and a communication unit 211. The mobile electronic device 220 includes a processing unit 120, a second communication unit 221 and a storage unit 130. The wearable device 210 and the mobile electronic device 220 are connected and communicate with each other via the first communication unit 211 and the second communication unit 221. In an embodiment, the first communication unit 211 and the second communication unit 221 are wireless communication modules that support wireless communication protocols such as Wi-Fi, WiMAX, 3GPP standards and Bluetooth. In another embodiment, the first communication unit 211 and the second communication unit 221 are wired communication modules via Ethernet or optical fiber, which is not limited herein.

Steps of the method for detecting physiological information are described below cooperating with the physiological information detecting device 10. The operation principle of the physiological information detecting system 20 is the same.

Figure 3:
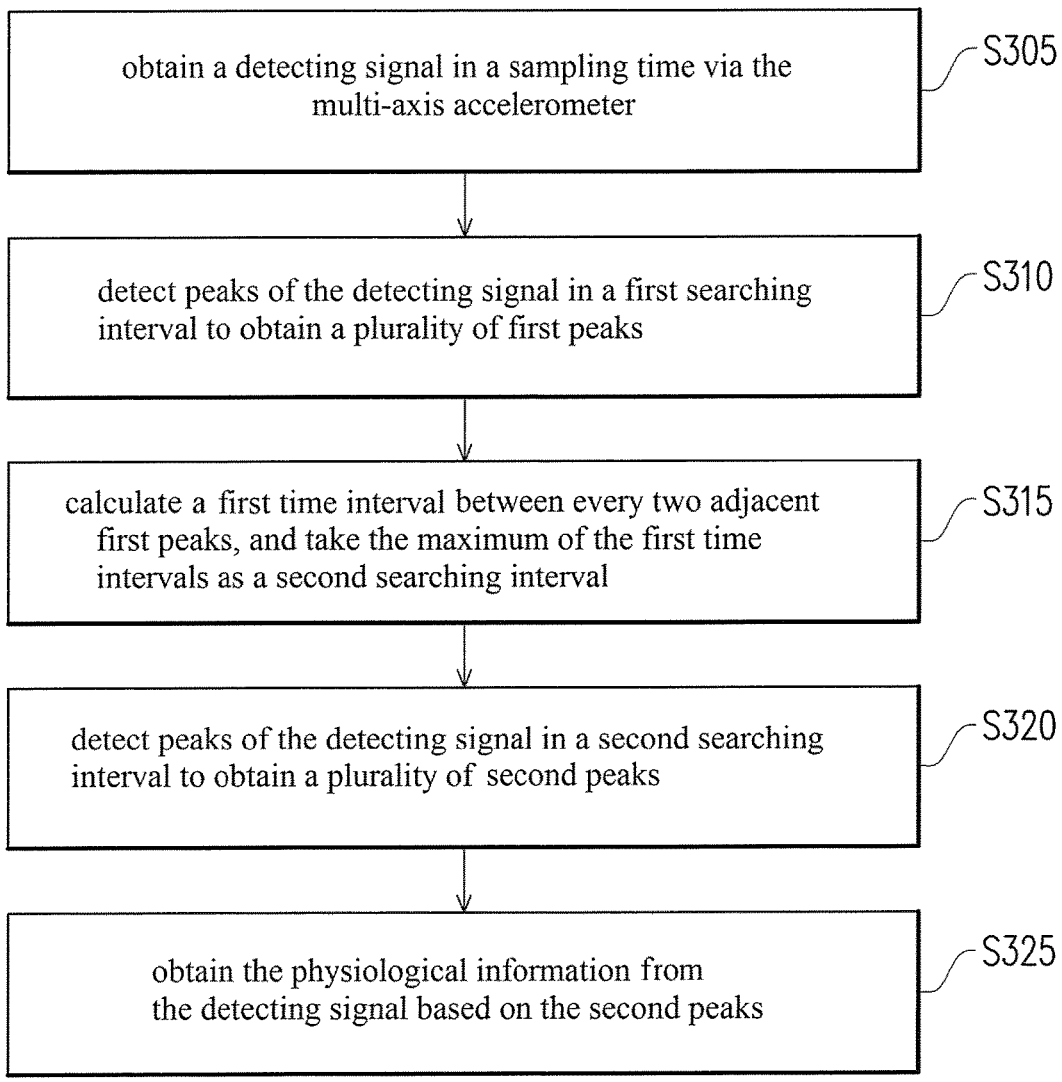
FIG. 3 is a flowchart showing a method for detecting the physiological information in an embodiment.

FIG. 3 is a flowchart of a method for detecting physiological information in an embodiment. Referring to FIG. 1 and FIG. 3, in step S305, the multi-axis accelerometer 110 obtains a detecting signal in a sampling time. In the embodiment, the detecting signal is a Z-axis signal extracted from the acceleration data generated by the multi-axis accelerometer 110. In another embodiment, the detecting signal is a sum signal of an X-axis signal, a Y-axis signal and a Z-axis signal derived from the acceleration data generated by the multi-axis accelerometer 110. The detecting signal is extracted from the acceleration data depending on the required physiological information. For example, if a heart rate is required, the Z-axis signal is extracted as the detecting signal; if a respiratory rate is required, the X-axis signal, the Y-axis signal and the Z-axis signal are extracted and added as the detecting signal.

In step S315, the peak-detecting module 150 calculates a first time interval between every two adjacent first peaks, and takes the maximum of the first time intervals as a second searching time interval. In step S320, the peak-detecting module 150 detects peaks of the detecting signal in the second searching time interval to obtain a plurality of second peaks. In the embodiment, the second searching time interval is larger than the first searching time interval. Through step S315 and step S320, peaks that do not represent the physiological information are excluded. In step S325, the physiological information estimation module 160 obtains the physiological information in the detecting signal based on the second peaks.

An embodiment for detecting a heart rate is described below in combination with FIG. 3.

In the embodiment, for the accuracy of the heart rate, after the detecting signal is obtained (step S305), a Z-axis signal is preprocessed after the Z-axis signal is extracted from the acceleration data, and the preprocessed Z-axis signal is served as the detecting signal. That is, the signal-obtaining module 140 obtains an acceleration data in a sampling time (such as 30 sec or 1 min) via the multi-axis accelerometer 110, and extracts the Z-axis signal from the acceleration data. Subsequently, the signal-obtaining module 140 amplifies the Z-axis signal. In an embodiment, the signal-obtaining module 140 performs the square of the Z-axis signal to amplify the signal representing the robust heartbeats. Then, the signal-obtaining module 140 filters the amplified Z-axis signal to obtain the detecting signal. In an embodiment, the signal-obtaining module 140 uses a band pass filter to filter out unexpected high-frequency and low-frequency data from the Z-axis signal, and then only the signal data within a preset range is kept. In an embodiment, the signal data in the range of 1~10 Hz are kept. The step of filtering process excludes the low-frequency signal (for example, waves generated by respirations or slight motions) and the high-frequency noise signal from the amplified Z-axis signal.

Figure 4A:
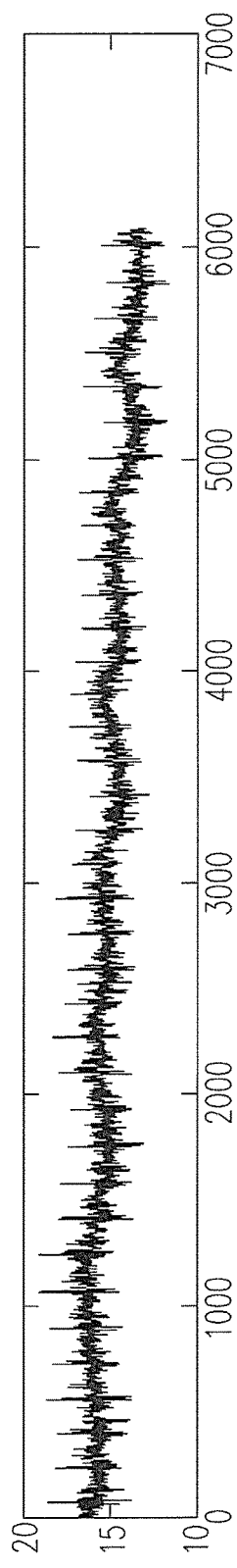
FIGS. 4A-4C are schematic diagrams showing preprocessings to a signal in an embodiment.
Figure 4B:
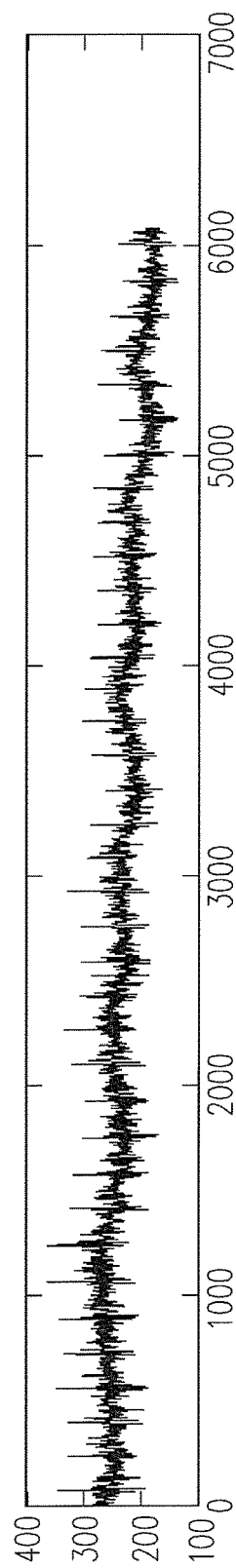
Figure 4C:
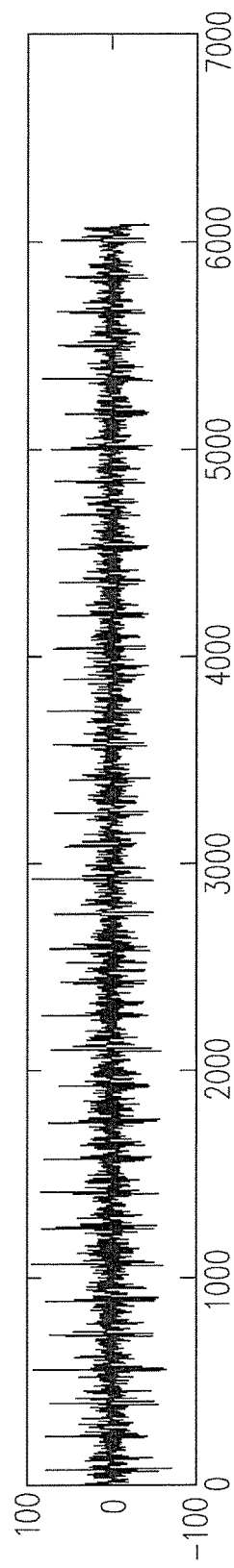

FIGS. 4A-4C are schematic diagrams showing the preprocessings to the signal in an embodiment. FIG. 4A shows a raw data of the Z-axis signal generated by the multi-axis accelerometer 110 in a sampling time of 30 sec. FIG. 4B shows an amplified signal derived from the raw data (for example, after the square calculation). FIG. 4C shows a detecting signal filtered by a LPF based on the amplified signal in FIG. 4B. In the embodiment, the horizontal axis indicates the amount of the sampling points and the vertical axis indicates the variation per unit time. Then, the peak-detecting module 150 detects the peaks of the detecting signal as shown in FIG. 4C (steps S310~S320).

Figure 5:
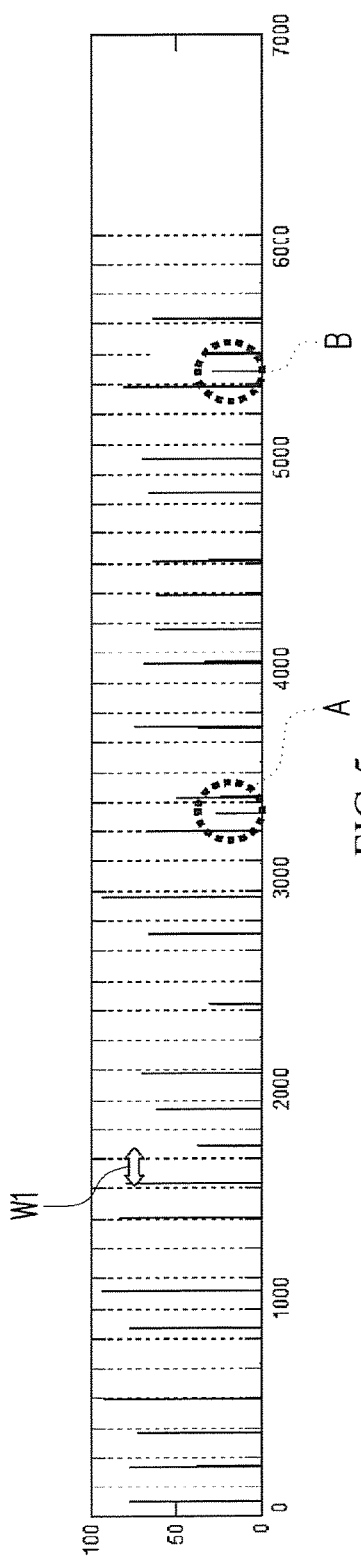
FIG. 5 is a schematic diagram showing a plurality of first peaks in an embodiment.

The peak-detecting module 150 detects the peaks of the detecting signal in a first searching time interval to obtain a plurality of the first peaks. FIG. 5 is a schematic diagram showing a plurality of first peaks in an embodiment. In the embodiment, the peak-detecting module 150 takes a detecting window of 200 ms which is indicated by a dotted line in FIG. 5, and the peak-detecting module 150 detects the peaks of the detecting signal every 200 ms to find out a maximum peak value (i.e., the first peak) in each detecting window. That is, peaks are detected in every 200 ms to obtain the first peaks.

Figure 6:
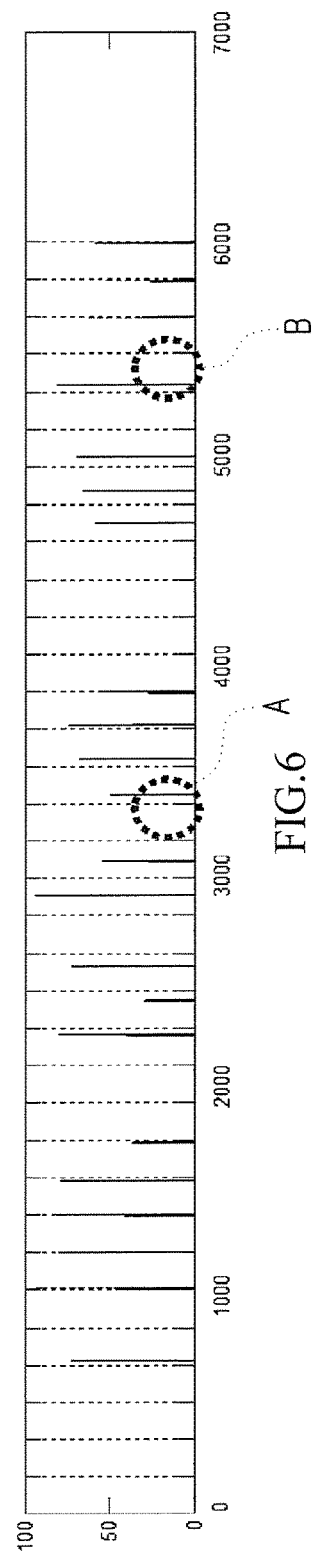
FIG. 6 is a schematic diagram showing a plurality of second peaks in an embodiment.

As for the plurality of first peaks as shown in FIG. 5, the peak-detecting module 150 calculates time intervals between every two adjacent first peaks to find a maximum time interval as a second searching time interval W1. In the embodiment, the second searching time interval is 825 ms. Then, the peak-detecting module 150 detects the peaks of the detecting signal in every new detecting window of 825 ms to find out a maximum peak value (i.e., the second peak) in each detecting window. FIG. 6 is a schematic diagram showing the plurality of second peaks in an embodiment.

Small peaks that do not represent the heartbeats are excluded by detecting peaks in two different detecting windows. Referring to FIGS. 5 and 6, it assumes that the first peaks in selected circles A and B in FIG. 5 do not represent the heartbeats. After the first peaks in every first detecting window are detected, the peak-detecting module 150 obtains a second searching time interval W1 and detects the peaks of the detecting signal again in the second searching time interval W1. Thus, as shown in FIG. 6, the peaks in the selected circles A and B would not be detected as the peaks by the peak-detecting module 150.

Then, the physiological information estimation module 160 obtains the physiological information from the detecting signal based on the second peaks, i.e., the heart rate in every minute. The physiological information estimation module 160 calculates a second time interval between every two adjacent second peaks and determines whether to apply a compensation calculation according to the second time intervals. If a difference between any two second time intervals is less than a preset threshold, the physiological information estimation module 160 accumulates the number of the second peaks directly as the heart rate. In an embodiment, if one of the second time intervals is more than a preset interval, or if two successive second time intervals are both within a preset interval range, the compensation calculation is performed on the total value of the second peaks.

Figure 7:
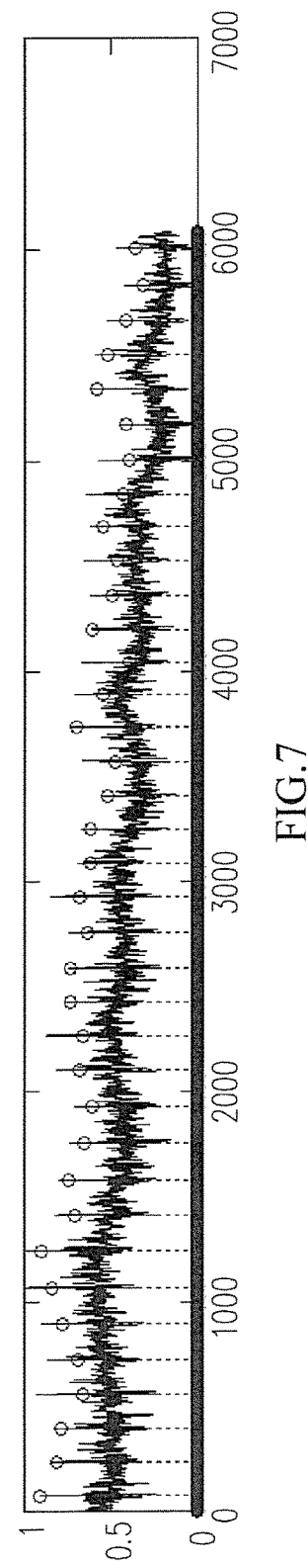
FIG. 7 is a schematic diagram showing a final detecting result in an embodiment.
Figure 8:
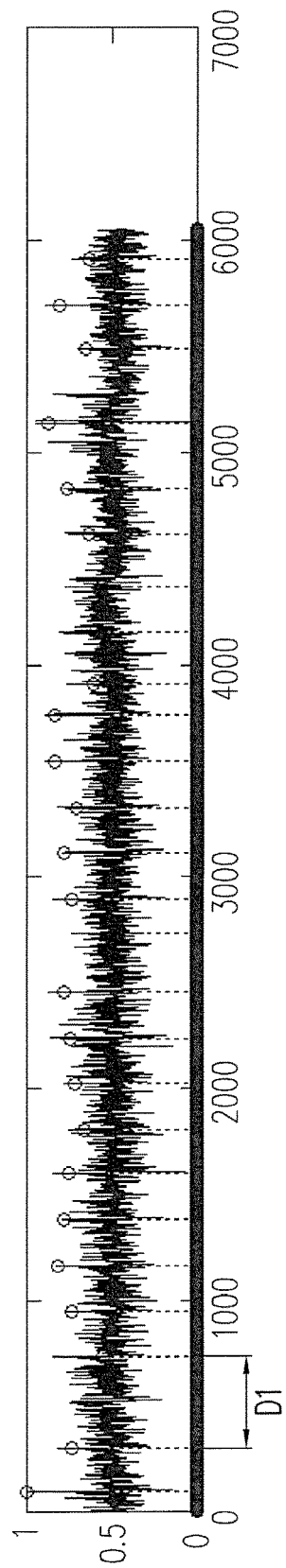
FIG. 8 is a schematic diagram showing a final detecting result in an embodiment.
Figure 9:
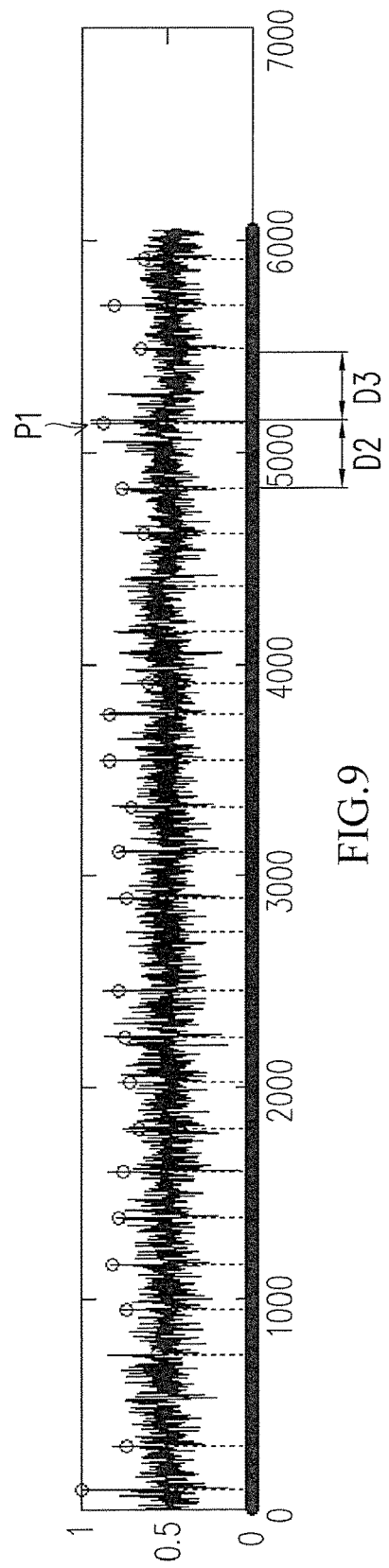
FIG. 9 is a schematic diagram showing a final detecting result in an embodiment.

An embodiment for calculating the heart rate is provided below. FIG. 7 is a schematic diagram showing a final detecting result in an embodiment. FIG. 8 is a schematic diagram showing a final detecting result in an embodiment. FIG. 9 is schematic diagram showing a final detecting result in an embodiment. The detected second peaks are shown in circles as shown in FIGS. 7-9.

In FIG. 7, the time intervals between every two second peaks are average. After the second time intervals between every two adjacent second peaks are calculated, the physiological information estimation module 160 further determines whether the difference between any two second time intervals is less than a preset threshold (in an embodiment the preset threshold is 100 ms). If all the differences between any two second time intervals are less than a preset threshold (which means the time intervals between every two adjacent second peaks are similar or substantially the same), the heart rate is obtained by accumulating the number of the second peaks directly.

As shown in FIG. 8, the physiological information estimation module 160 determines whether each of the second time intervals between every two adjacent second peaks is more than a preset interval. In the embodiment, the preset interval is set depending on the second searching time interval and a preset constant. In an embodiment, the preset interval is equal to 1.4 times of the second searching time interval. If one of the second time intervals (D1 as shown in FIG. 8) is more than the preset interval, it is possible that a peak representing a heartbeat in the second time interval (which is larger than the preset interval) is missed. Therefore, the physiological information estimation module 160 applies a compensation calculation on the total value of the second peaks to obtain the heart rate. In an embodiment, in the case of a sampling time of 30 sec, the heart rate S in every one minute is expressed as follows: $S=(sum[P]+1)\times 2$, wherein sum[P] represents the total value of the second peaks in the sampling time of 30 sec.

In FIG. 9, the physiological information estimation module 160 determines whether each of the second time intervals is within a preset interval range. In the embodiment, an upper limit and a lower limit of the preset interval range are set depending upon the second searching time interval, a first and a second constant. In an embodiment, the preset interval range is 1.1 to 1.4 times of the second searching time interval. If both of the two successive second time intervals (D2, D3 as shown in FIG. 9) are within the preset interval range, the physiological information estimation module 160 applies a compensation calculation on the total value of the second peaks to obtain the heart rate.

If both of the two successive second time intervals D2, D3 are within the preset interval range, it is possible that a second peak P1 (which does not represent the heartbeat) is mistakenly taken as the peak representing the heartbeat. In other words, two real peaks that represent the heartbeats are possibly missed in the two successive second time intervals D2, D3. Therefore, in the case of the sampling time of 30 sec, the heart rate S in every minute is expressed as follows: $S=(sum[P]-1+2)\times 2=(sum[P]+1)\times 2$, wherein sum[P] represents the total value of the second peaks in the sampling time of 30 sec.

In addition to the heart rate, the physiological information detecting device 10 is also used for detecting a respiratory rate. An embodiment for detecting the respiratory rate is illustrated below with references to FIG. 3.

Referring to FIG. 1, the signal-obtaining module 140 obtains the X-axis signal, the Y-axis signal and the Z-axis signal in a sampling time via the multi-axis accelerometer 110, and then adds the X-axis signal, the Y-axis signal and the Z-axis signal to obtain the detecting signal.

Figure 10A:
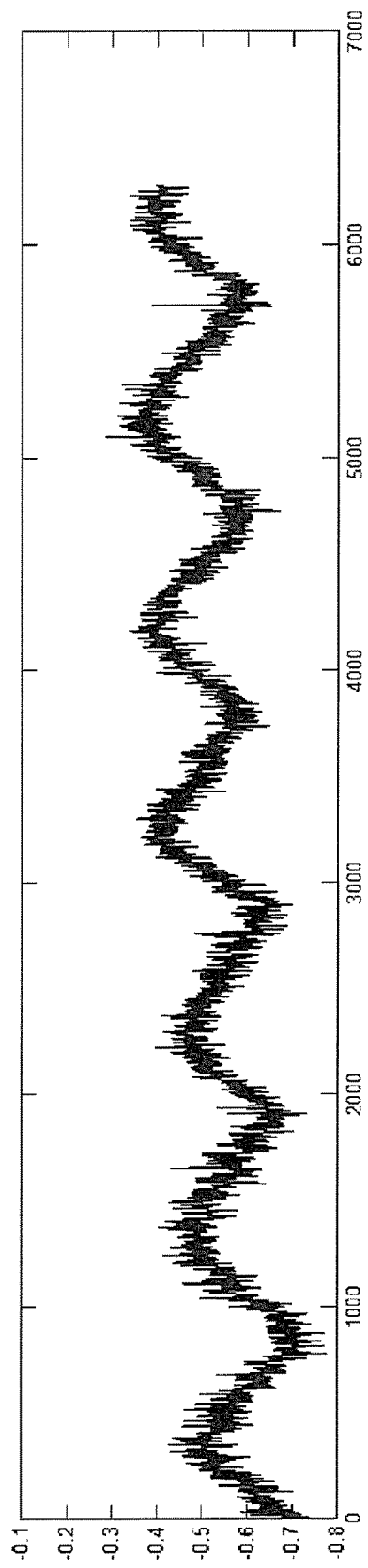
FIGS. 10A-10H are schematic diagrams showing processes for detecting a respiratory rate in an embodiment.
Figure 10B:
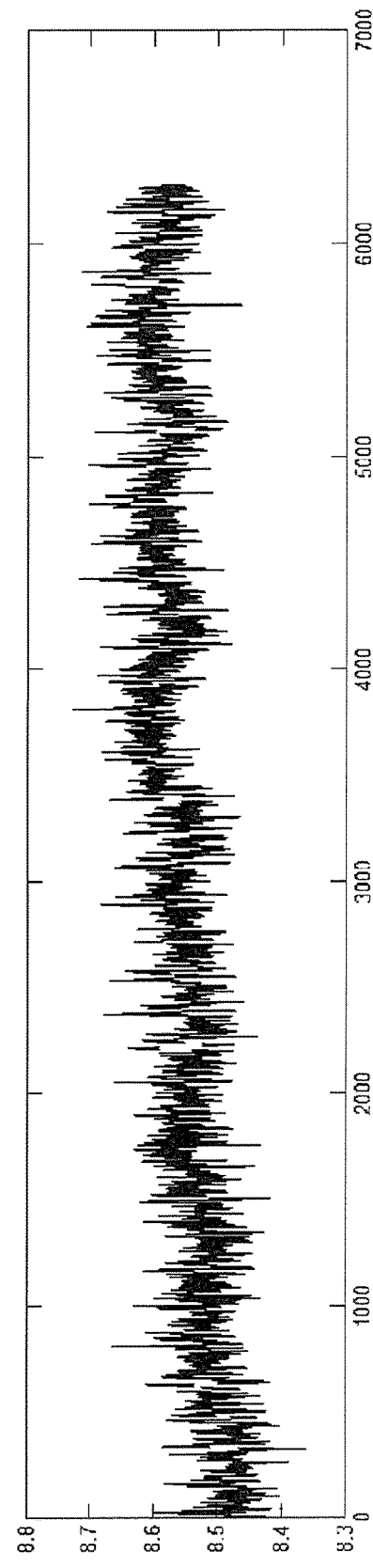
Figure 10C:
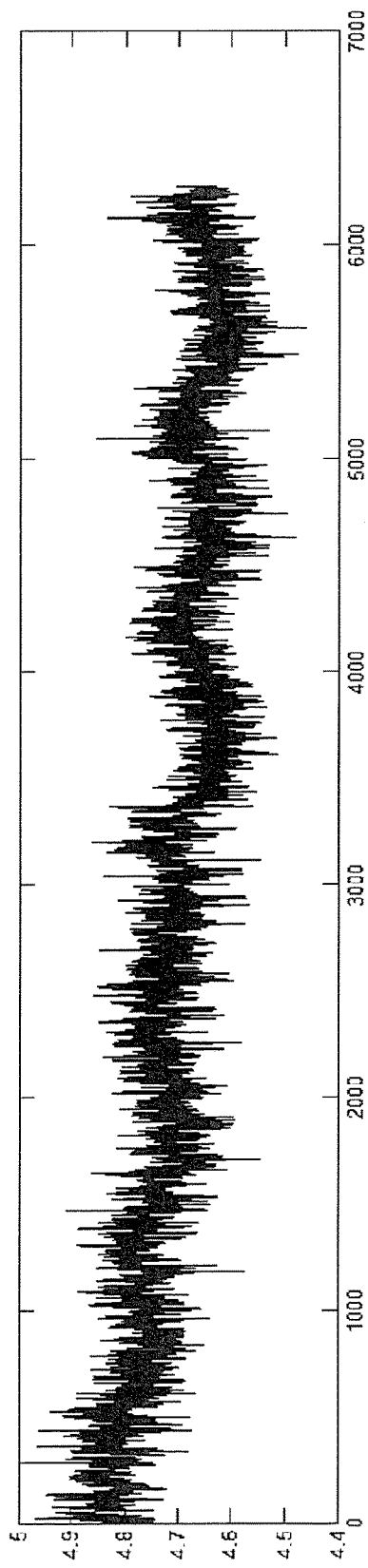
Figure 10D:
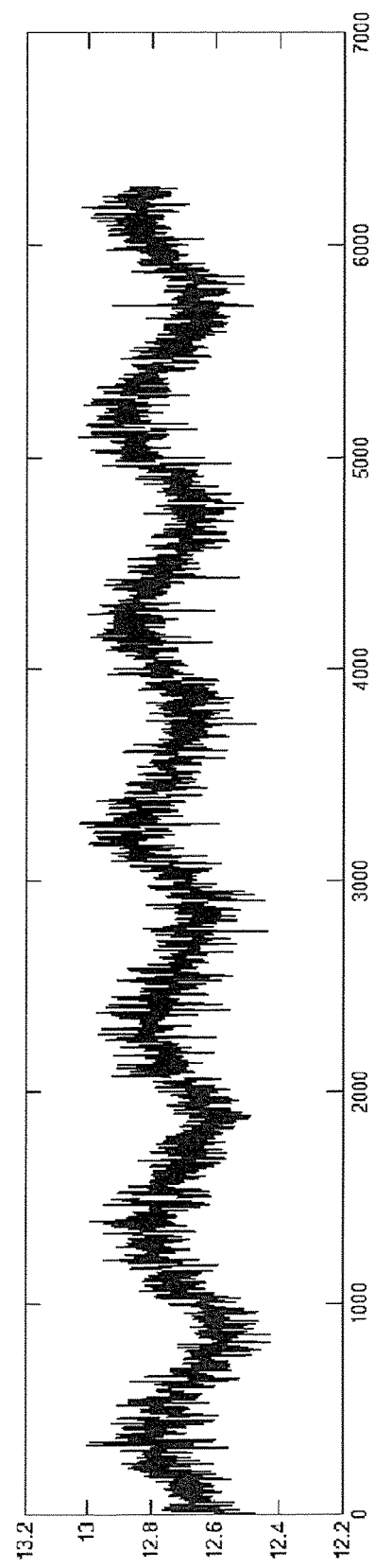

FIGS. 10A-10H are schematic diagrams showing the processes for detecting the respiratory rate in an embodiment. In the embodiment, the horizontal axis indicates the number of the sampling points, and the vertical axis indicates the variation per time unit. FIGS. 10A-10H show the variation of the X-axis signal, the Y-axis signal and the Z-axis signal, respectively. The signal-obtaining module 140 adds the X-axis signal, the Y-axis signal and the Z-axis signal (as shown in FIGS. 10A-10C) generated by the multi-axis accelerometer 110 to obtain the detecting signal (as shown in FIG. 10D).

Figure 10E:
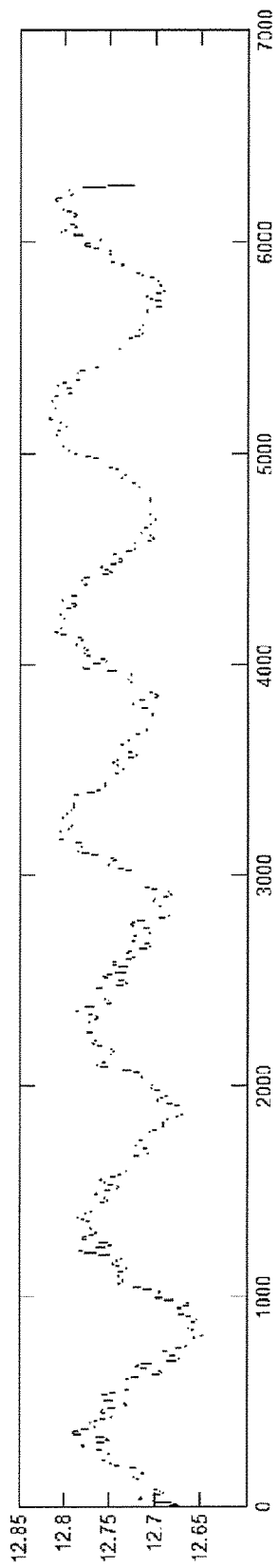

The signal-obtaining module 140 preprocesses the detecting signal for the accuracy of the respiratory rate. Since the signal representing the respiratory lies in the low frequency region, the signal-obtaining module 140 filters the detecting signal by utilizing a low pass filter to remain the low-frequency signal (for example, 0~1 Hz). A filtered signal is obtained as shown in FIG. 10E. Then, the signal-obtaining module 140 smoothes the filtered detecting signal (as shown in FIG. 10E) via a mean filter. Thus, a smoothed detecting signal is obtained as shown in FIG. 10F.

Figure 10F:
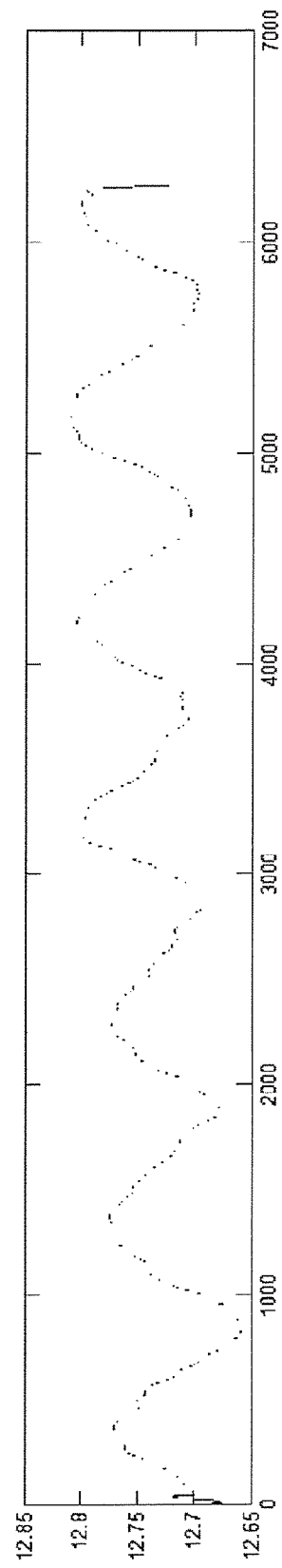

Then, the peak-detecting module 150 detects the peaks of the detecting signal as shown in FIG. 10F. In the embodiment, the peak-detecting module 150 finds out the first peaks of the detecting signal as shown in FIG. 10F using a small detecting window. In an embodiment, the sampling frequency is 250 times per second. Then, the detecting window is initially set as $125(250\times 0.5=125)$ sampling points, which represents that 125 data is in one detecting window. The peak-detecting module 150 detects peaks in every detecting window, and finds out the maximum peak values (i.e., multiple first peaks) in every 125 sampling points orderly, as shown in FIG. 10G.

Figure 10G:
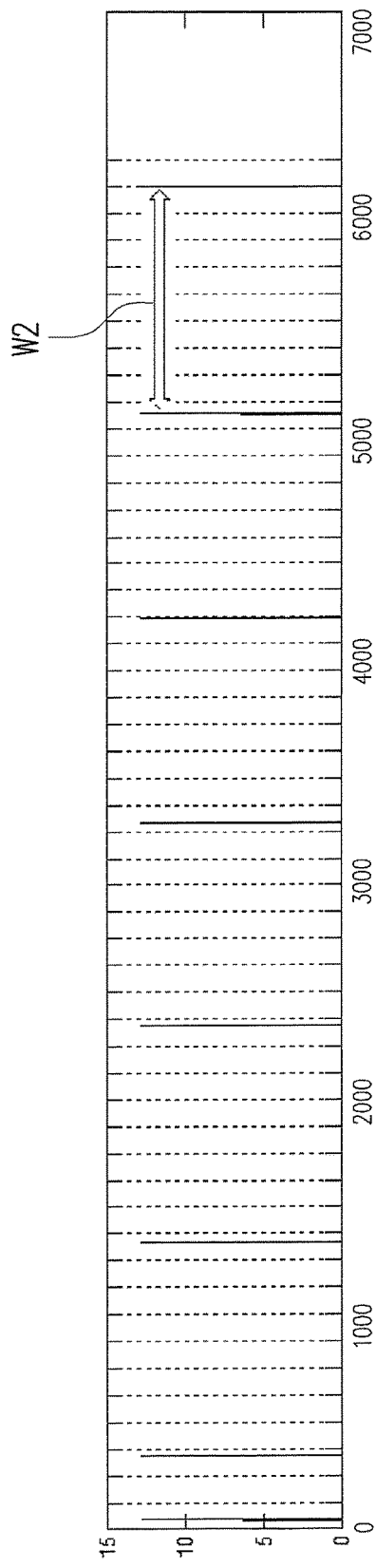
Figure 10H:
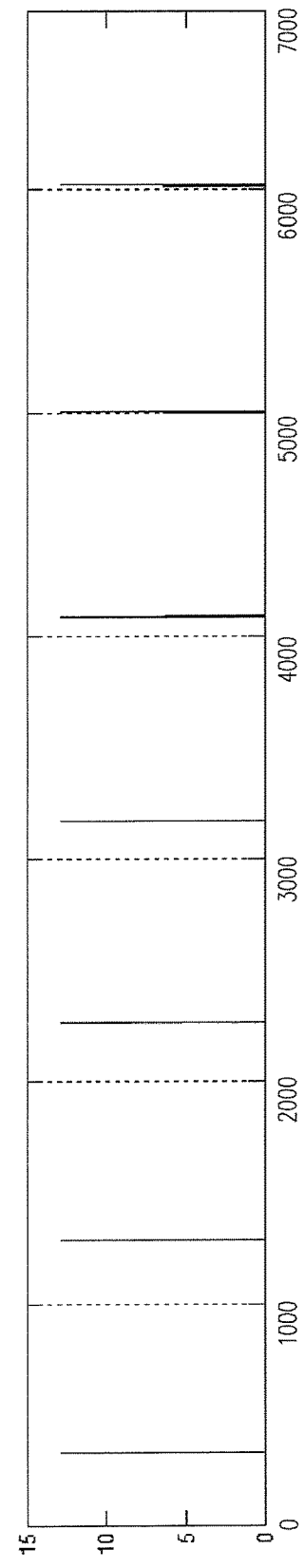

Then, the peak-detecting module 150 calculates time intervals (first time intervals) between every two adjacent first peaks as shown in FIG. 10G, to finds out the maximum of the first time intervals as a second searching time interval W2 (a new detecting window). Then, the peak-detecting module 150 searches peaks in the second searching time interval W2 to obtain multiple second peaks as shown in FIG. 10H. Then, the physiological information estimation module 160 calculates the respiratory rate in one minute based on the second peaks. A compensation calculation for calculating the respiratory rate is similar to that for calculating the heart rate above, which can be referred to the descriptions with respect to FIGS. 7-9 and omitted herein.

Furthermore, in an embodiment, the steps of the method for detecting the physiological information are implemented by the physiological information detecting system 20. The acceleration data is transmitted from the wearable device 210 to the mobile electronic device 220 via the first communication unit 211, and then the steps are implemented by the mobile electronic device 220.

In sum, a multi-axis accelerometer (such as a gravitational accelerometer) is utilized to obtain the physiological information (such as a heart rate or a respiratory rate). Since the gravitational accelerometer is disposed in a mobile electronic device, no more cost is needed. Moreover, no more space is needed for accommodating the gravitational accelerometer.

Although the disclosure has been disclosed with reference to certain preferred embodiments thereof, the disclosure is not for limiting the scope. Persons having ordinary skill in the art may make various modifications and changes without departing from the spirit and the scope of the disclosure. Therefore, the scope of the appended claims should not be limited to the description of the preferred embodiments described above.

What is claimed is:

1. A method for detecting physiological information, for a physiological information detecting device having a processor and a wearable multi-axis accelerometer, the method comprises:
   obtaining, by the processor, an acceleration data in a sampling time via the multi-axis accelerometer and filtering the acceleration data by a filter to obtain a detecting signal at a preset frequency range;
   detecting, by the processor, peaks of the detecting signal in a first searching time interval to find out a plurality of first peaks;
   calculating, by the processor, first time intervals between every two adjacent first peaks, and finding a maximum time interval from the first time intervals as a second searching time interval;
   detecting, by the processor, peaks of the detecting signal in the second searching time intervals to find out a plurality of second peaks; and
   calculating, by the processor, the physiological information from the detecting signal based on the second peaks.

2. The method for detecting physiological information according to claim 1, wherein the step of calculating the physiological information from the detecting signal based on the second peaks includes:
   calculating a second time interval between every two adjacent second peaks, and
   accumulating the number of the second peaks as the physiological information when a difference between any two second time intervals is less than a preset threshold.

3. The method for detecting physiological information according to claim 1, wherein the step of calculating the physiological information from the detecting signal based on the second peaks includes:
   calculating a second time interval between every two adjacent second peaks,
   determining whether each of the second time intervals exceeds a preset interval, wherein the preset interval depends on the second searching time interval and a preset constant; and
   applying a compensation calculation to the total value of the second peaks to calculate the physiological information when one of the second time intervals exceeds the preset interval.

4. The method for detecting physiological information according to claim 1, wherein the step of calculating the physiological information from the detecting signal based on the second peaks includes:
   calculating a second time interval between every two adjacent second peaks,
   determining whether each of the second time interval is within a preset interval range, wherein an upper limit and a lower limit of the preset interval range depend on the second searching time interval, a first constant and a second constant, and
   applying a compensation calculation to the total value of the second peaks to calculate the physiological information when both of the two successive second time intervals are within the preset interval range.

5. The method for detecting physiological information according to claim 1, wherein the step of obtaining the acceleration data in the sampling time via the multi-axis accelerometer and filtering the acceleration data by the filter to obtain the detecting signal at the preset frequency range includes:
   extracting a Z-axis signal from the acceleration data;
   amplifying the Z-axis signal; and
   filtering the amplified Z-axis signal by the filter to obtain the detecting signal.

6. The method for detecting physiological information according to claim 1, wherein the step of obtaining the detecting signal in the sampling time via the multi-axis accelerometer includes:
   obtaining an X-axis signal, a Y-axis signal and a Z-axis signal in the sampling time via the multi-axis accelerometer;
   adding the X-axis signal, the Y-axis signal and the Z-axis signal to obtain the detecting signal.

7. The method for detecting physiological information according to claim 1, wherein the physiological information is a heart rate or a respiratory rate.

8. A wearable physiological information detecting device, comprising:
   a multi-axis accelerometer; and
   a processor coupled to the multi-axis accelerometer,
   wherein the processor controls a signal-obtaining module to obtain an acceleration data in a sampling time via the multi-axis accelerometer and to filter the acceleration data by a filter to obtain a detecting signal at a preset frequency range;
   the processor controls a peak-detecting module to detect peaks of the detecting signal in a first searching time interval to find out a plurality of first peaks, calculate first time intervals between every two adjacent first peaks, and find a maximum time interval from the first time intervals as a second searching time interval, and detect peaks of the detecting signal in the second searching time interval to find out a plurality of second peaks; and the processor controls a physiological information estimation module to calculate the physiological information from the detecting signal based on the second peaks.

9. The wearable physiological information detecting device according to claim 8, wherein the physiological information estimation module calculates a second time interval between every two adjacent second peaks, when the difference between any two second time intervals is less than the preset threshold, the physiological information estimation module accumulates the number of the second peaks as the physiological information.

10. The wearable physiological information detecting device according to claim 8, wherein the physiological information estimation module calculates the second time intervals between every two adjacent second peaks, and determines whether each of the second time intervals exceeds a preset interval, the preset interval depends on the second searching time interval and a preset constant; when one of the second time intervals exceeds the preset interval, the physiological information estimation module applies a compensation calculation to the total value of the second peaks to calculate the physiological information.

11. The wearable physiological information detecting device according to claim 8, wherein the physiological information estimation module calculates a second time interval between every two adjacent second peaks and determines whether each of the second time intervals is within a preset interval range, an upper limit and a lower limit of the preset interval range depend on the second searching time interval, a first constant and a second constant, when both of the two successive second time intervals are within the preset interval range, the physiological information estimation module applies a compensation calculation to the total value of the second peaks to calculate the physiological information.

12. The wearable physiological information detecting device according to claim 8, wherein the signal-obtaining module extracts a Z-axis signal from the acceleration data, amplifies the Z-axis signal, and filters the amplified Z-axis signal to obtain the detecting signal.

13. The wearable physiological information detecting device according to claim 8, wherein the signal-obtaining module obtains an acceleration data in the sampling time via the multi-axis accelerometer, and adds an X-axis signal, a Y-axis signal and a Z-axis signal derived from the acceleration data to obtain the detecting signal.

14. A physiological information detecting system, comprising:

a wearable device for detecting physiological information, including:

a multi-axis accelerometer for generating an acceleration data in a sampling time; and a first communication device coupled to the multi-axis accelerometer; and a mobile electronic device including:

a second communication device connected with the first communication device;

a processor coupled to the second communication device, receiving the acceleration data from the wearable device via the second communication device, wherein the processor controls a signal-obtaining module to obtain a detecting signal from filtering the acceleration data by a filter at a preset frequency range;

the processor controls a peak-detecting module to detect peaks of the detecting signal in a first searching time interval to find out a plurality of first peaks, calculate a first time interval between every two adjacent first peaks, and find a maximum time interval from the first time intervals as a second searching time interval, and detect peaks of the detecting signal in the second searching time interval to find out a plurality of second peaks; and the processor controls a physiological information estimation module to calculate the physiological information from the detecting signal based on the second peaks.

* * * * *